United States Patent [19]

Lizardi

[11] Patent Number: 5,059,294
[45] Date of Patent: Oct. 22, 1991

[54] METHOD FOR SEPARATING NUCLEIC ACIDS AND NUCLEIC ACID PROBES

[75] Inventor: Paul M. Lizardi, Bronx, N.Y.

[73] Assignee: The University of Puerto Rico, P.R.

[21] Appl. No.: 77,901

[22] Filed: Nov. 16, 1987

Related U.S. Application Data

[63] Continuation of Ser. No. 813,662, Dec. 26, 1985.

[51] Int. Cl.[5] .................... B01D 57/02; G01N 27/26
[52] U.S. Cl. ........................... 204/182.8; 204/299 R
[58] Field of Search ...................... 204/299 R, 182.8

[56] References Cited

U.S. PATENT DOCUMENTS 4,473,452  9/1984  Cantor et al. ............... 204/299 RX

FOREIGN PATENT DOCUMENTS 8702133  4/1987  PCT Int'l Appl. ............ 204/299 R

OTHER PUBLICATIONS

G. F. Carle and M. V. Olson, "Separation of chromosomal DNA molecules from year by orthogonal-field-alternation gel electrophoresis" Nucleic Acids Research, vol. 12, No. 14 (1984) pp. 5647-5664.

Primary Examiner—John F. Niebling
Assistant Examiner—John S. Starsiak
Attorney, Agent, or Firm—Ostrolenk, Faber & Gerb

[57] ABSTRACT

An improved method and device for nucleic acid hybridization assay employing combined direct an alternating field electrophoresis are disclosed. In the method of the present invention, a sample is hybridized with nucleic acid probe and is contacted with a support medium where direct and alternating electric fields are applied. Under the influence of the electric fields, hybrid separates from non-specifically bound nucleic acid probe. The hybrid may be measured on the support medium itself as on a paper strip or in a cartridge containing support medium or may be blotted on an inert surface and then measured. The method an device are useful in the diagnosis of diseases. Kits are provided for assay of a large number of diseases.

2 Claims, 3 Drawing Sheets

TIME-PHASE DIAGRAM APPLIED ELECTRIC FIELDS

TIME-PHASE DIAGRAM APPLIED ELECTRIC FIELDS

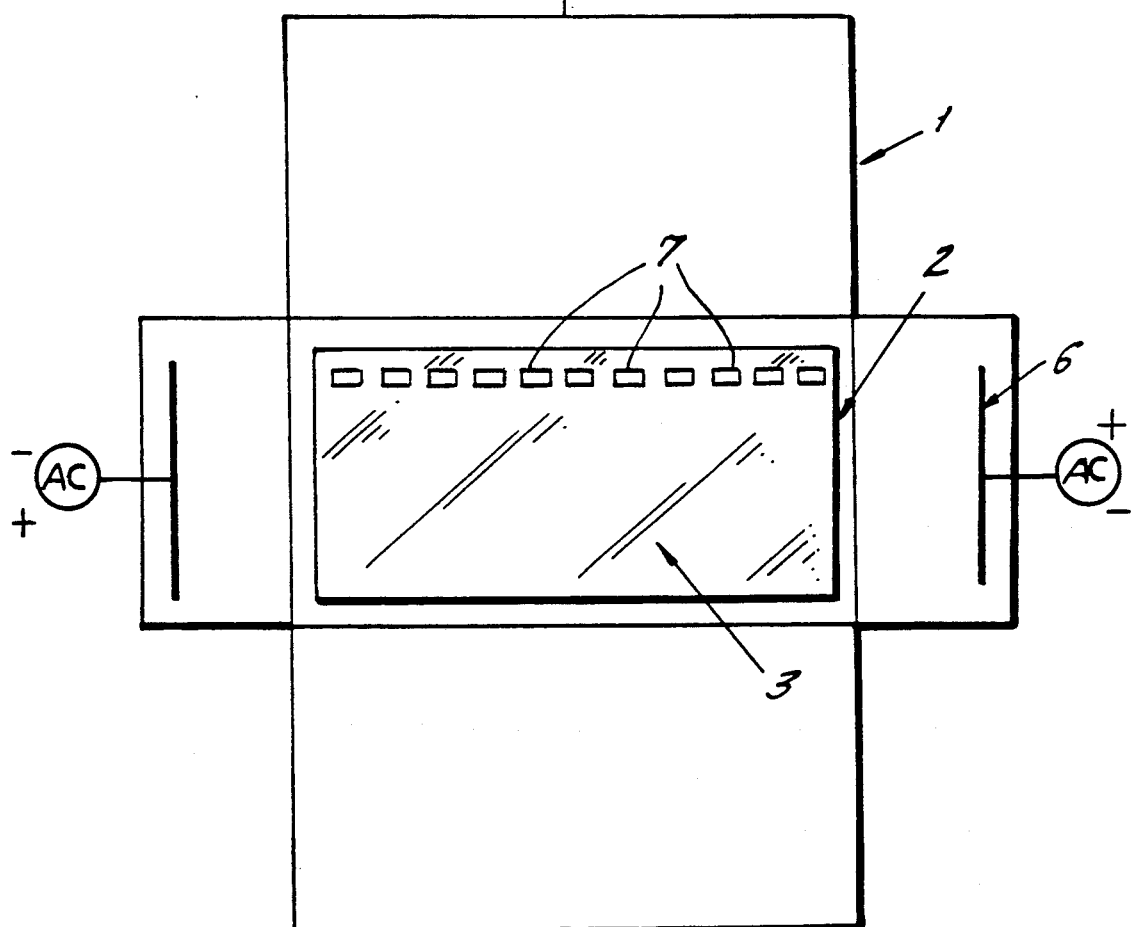
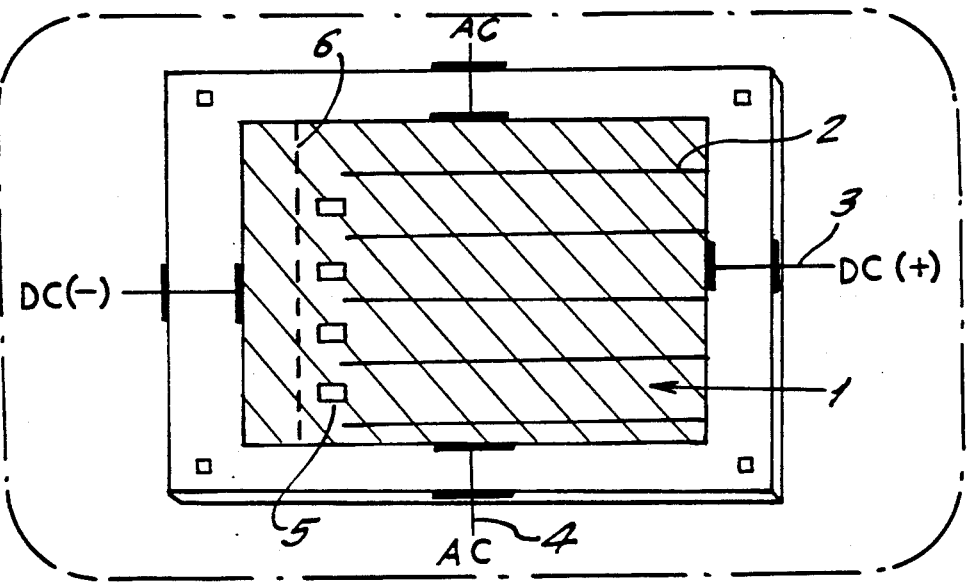

METHOD FOR SEPARATING NUCLEIC ACIDS AND NUCLEIC ACID PROBES

This application is a continuation-in-part of U.S. patent application Ser. No. 813,662 filed Dec. 26, 1985.

BACKGROUND OF THE INVENTION

This invention concerns methods and devices for separating nucleic acid from substances to which it is bound non-specifically utilizing combined direct and alternating field electrophoresis. The devices and methods are useful for rapid diagnosis of disease.

The discovery of the helical structure of DNA made possible the comparison of DNA in the genomes of various species. It was soon discovered that in the cells of each species there are segments of DNA comprised of nucleotide sequences unique to that species. Furthermore it was found that viruses also contain unique segments of DNA. These unique segments provide the basis for a new technology and promise a new solution to the problem of detecting living organisms in biological specimen. They will be especially important in the diagnosis of diseases caused by pathogenic organisms (Falkow, S. et al. U.S. Pat. No. 4,348,535).

In this technology a "probe", a segment of single-stranded nucleic acid which is complementary to a specific DNA, is used to identify a cell or virus in a sample. The probe is put into contact with the sample and is allowed to react by base pairing to form a double-stranded hybrid with any complementary single-stranded DNA which is present. This hybrid is then separated from the sample and any unreacted probe. Reaction is followed by means of a label, a radioactive or chromophoric group, for example, on the hybrid.

Separation of hybrid from probe has been a fundamental obstacle in the development of this technology. This step, as presently practiced, is time consuming, laborious, and may lead to erroneous results.

Initial efforts to separate hybrid and probe have been directed towards immobilizing the hybrid on an inert surface which can be washed to remove probe from the sample being analyzed. It was known that DNA in solution, in its naturally occurring double-stranded form, can be denatured, that is, separated into two separate strands, and then again renatured simply by manipulating the temperature as well as the ionic strength and pH of the solution. Single-stranded DNA can similarly be caused to react with single-stranded RNA in solution to form a double-stranded hybrid. (C. L. Schildkraut, J. Marmur, J. Fresco and P. Doty, J. Biol. Chem. 236, 803 (1961; B. D. Hall and S. Spiegelman, Proc. Nat'l. Acad. Sci. USA 47, 137 (1961). Gillespie and Spiegelman (D. Gillespie and S. Spiegelman, J. Mol. Biol. 12, 829 (1965)) were able to immobilize single-stranded DNA on nitrocellulose and found that the immobilized DNA was able to react with DNA or RNA in solution to form an immobilized hybrid. This became the basis of a workable separation technique. Other researchers, notably Bernardi (G. Bernardi, Nature 206, 779 (1965)) and Kohne (D. E. Kohne, Biophys. J. 8, 1104 (1968)) found that hydroxyl apatite 15 binds double-stranded hybrids but not nucleic acid. They used the hydroxyl apatite to "fish" hybrids from solution.

These two traditional methods of separating double-stranded nucleic acid hybrids from single-stranded probes have aided the study of nucleic acids in the laboratory, but have not proven useful in clinics where repeated diagnoses must be performed. Long times are required for each analysis which involves multiple washing steps and other manipulations, and a high level of skill is needed to make the methods operative.

Because of the inherent problems of the immobilization technique, a novel enzymatic approach was attempted. It was found that S1 nuclease is capable of digesting single-stranded chains of RNA and DNA into nucleotides, but the enzyme does not attack the double-stranded forms (Leong, J. A., Gerapin, A. C., Jackson, N., Fanshier, Ll, Levinson, W. and Biship, J. M. (1972) J. Virol., 891). The enzyme may thus be used to remove interfering single-stranded probes from the hybrid. This procedure has proven useful in the hands of researchers "with good hands" but has not found acceptance in more routine applications because the enzyme is difficult to control, is sensitive to small buffer changes and results have been difficult to reproduce.

Rosbash (Rosbash, M., et al., In "Methods in Enzymology" Vol. 68, pp. 454–469 (1979)) has attempted to separate nucleic acids by utilizing their size differences. He was able to separate single-stranded from double-stranded nucleic acids by gel filtration on agarose beads. However, this method, again, is mostly a research technique since artifactual complexes such as background human DNA interfere with separation. Also, the size difference between single- and double-strands must be large to allow efficient separation. Although temperature jacketing increases separation, with this modification the method becomes too clumsy for routine use.

Schwarz and Cantor have used electrophoretic methods to separate large segments of DNA. They found, while analyzing chromosomes, that large segments of DNA may be separated from one another on an agarose bed by applying discontinuous pulsed field electric gradients to the agarose bed. This method is useful for separating large nucleic acid strands, but has not been useful for separating probes from hybrids.

In a hybridization assay, the small probes form true hybrids with a specific segment of nucleic acid through the binding of complementary base pairs, but the probes also tend to bind indiscriminately by other non-specific bonds to the larger setgments and also to other larger components normally found in biological specimen. There is no way in conventional electrophoretic methods, as there is in methods involving immobilized hybrids, to wash away the artifactual probe. As a result, false bands appear on the gel.

Accordingly, a simple, effective, rapid method for hybridization assays with effectual separation of artifactual nucleic acid probe from larger aggregates and hybrids has been sought.

SUMMARY OF THE INVENTION

The present invention provides a novel method and device for hybridization assay of nucleic acids. The method and device are especially suitable for rapid analysis of biological specimen for nucleic acid and for diagnosis of disease.

The device of the present invention may be used to separate nucleic acid from substances to which it is bound non-specifically. The device comprises support medium and means for maintaining alternating and direct electric fields which are applied to the support medium. The device is especially useful during hybridization assay of nucleic acid to separate hybridization probe from the substances to which the probe binds non-specifically, for example single-stranded or double-stranded nucleic acid or to the hybrid itself. It is useful for separating other substances, biopolymers, for example, often found in biological samples which may also bind non-specifically to the probe. The probe is preferably chemically synthesized RNA or DNA containing natural or modified derivatives of nucleotide bases, nick-translated DNA or single-stranded RNA or DNA.

Support medium in the device comprises preferably a mesh-like polymeric matrix material. More than one kind of material may be present. Most preferably polymeric matrix materials are agarose, cellulose acetate, polyacrylamide, dextran, agar or gelatin. The support medium may comprise, in addition, ionic salts and buffers for maintaining electric fields across the support medium and for maintaining conditions suitable for complementary base pairing between nucleic acids. In certain embodiments there may be one or more membrane sheets embedded in the support medium.

In preferred embodiments of the invention, the device may comprise means for regulating temperature of the support medium and means for agitating the support medium gently to facilitate hybridization. The temperature regulating means is preferably a temperature detection thermocouple connected to a microprocessor for control of voltage supply. The support medium may be agitated by a controlled speed rocking mechanism.

The device may comprise, in addition, an inert surface in contact with said support medium and means for causing hybrid and separated nucleic acid to move to the inert surface. In these embodiments of the invention, separated nucleic acid and hybrid are caused to move to the inert surface by means of a direct electric field having a directional axis essentially perpendicular to the plane of the inert surface. Most preferably, the inert surface is capable of being removed from the device for purposes of measuring hybrid thereon.

Support medium in the device may be maintained in position by a holder, most preferably a cartridge capable of being removed from the device. The device may comprise more than one chamber, a hybridization chamber, for example, and a separation chamber and the cartridge may be transferred from one chamber to the other at different stages of hybridization assay.

The cartridge of the device of the present invention comprises the support medium on an inert support. The cartridge is capable of being placed in the device in a position that allows application of electric fields. It may be removed from the device for ease of measurement of hybrid. In certain embodiments of the invention, cartridge may be placed initially in a separate chamber in the device where concentration of sample components and hybridization may take place. Alternatively, concentration and hybridization of sample may proceed in a separate container, preferably in one chamber of the device. Sample is then transferred to support medium in the separation chamber.

Most preferably the cartridge of the present invention comprises a strip of inert material, paper, for example. In these embodiments, support medium and hybridized sample are initially mixed in solution and then applied to the inert strip. The inert strip is then placed in the device of the present invention where electric fields are applied for the purpose of washing extraneous non-bound probes from the hybrid.

The support medium is preferably one or more mesh-like polymeric materials, most preferably agarose, cellulose acetate, polyacrylamide, dextran, agar or gelatin. Ionic salts and buffers may also be present in the cartridge and support medium. In certain embodiments of the invention, there may be one or more membrane sheets embedded in the support medium. In other embodiments, there may be wells in the medium for receiving sample to be assayed by means of the device.

In preferred embodiments of the invention, the cartridge comprises an inert surface of material in contact with the support medium. In these embodiments, the separated hybrid is forced to move to the inert surface, as by application of direct electric field, where hybrid may be measured. The inert surface is essentially perpendicular to the plane of the cartridge and essentially parallel to the axis of field of direct current applied during separation. The inert surface may be strips of material embedded in the medium itself or may comprise a flat plane of material covering the total area of the support medium. Preferably, the inert surface is removable from the cartridge after assay for ease of measurement and for storage of data.

The device of the present invention is especially useful for diagnosing disease in an individual when a characteristic nucleic acid is pathegnemonic of a disease. A biological sample from the individual is assayed by means of the present device for a specific nucleic acid. Infectious diseases may be diagnosed, for example, by assay of a biological specimen for nucleic acid from a pathogenic organism. Genetic disorders and autonomic diseases may be diagnosed by assay of human cellular material for nucleic acid characteristic of the disorder or disease. The device may also be used to monitor purity of biological products such as vaccines, cell cultures, blood products, and products of genetically engineered organisms. Contamination of foodstuffs by living organisms may also be measured by the present device.

In the method of the present invention, nucleic acid is separated from substances to which it is bound non-specifically. In the method, nucleic acid and substances to which it is bound non-specifically are contacted with support medium. Alternate electric field and direct electric field are applied to said support medium to disrupt non-specific binding and to cause separation.

Nucleic acid is preferably a hybridization probe and the substances to which it is bound non-specifically are single-stranded nucleic acid, double-stranded nucleic acid, aggregates of single- or double-stranded nucleic acid or hybrids comprised of nucleic acid specifically bound to probe. The hybridization probe is preferably chemically synthesized RNA or DNA containing natural or modified derivatives of the nucleotide bases, nick-translated DNA or single-stranded RNA or DNA.

Direct electric field and alternate electric field may be applied on essentially the same directional axis or on different axes. In preferred embodiments, the axes of the two fields are essentially perpendicular. The direct field and alternating electric field are preferably applied at different times to the support medium, most preferably alternately, but they may also be applied concurrently.

Nucleic acid may be detected in a sample by contacting the sample with hybridization probe under conditions suitable for reaction between said nucleic acid and the probe to form double-stranded nucleic acid hybrid and the probe bound non-specifically to the hybrid and to other components of the biological sample. The hybrid and non-specifically bound probe are contacted with the support medium. Direct and alternating electric fields are applied to the support medium to separate non-specifically bound probe from hybrid and from other components of the sample. The separated hybrid is then measured. In preferred embodiments of the invention, the separated hybrid is caused to move to an inert surface as by a direct electric field and is measured on the inert surface.

Hybrid may be formed in a reaction mixture prior to being contacted with support medium or it may be formed on the medium itself, in a separate well, for example. In certain embodiments of the invention, the biological sample to be assayed is treated to concentrate components of the sample, especially nucleic acid, prior to hybridization. The sample may, for example, be applied to the medium where direct and alternate electric currents are applied. One or more membrane sheets may be embedded in the medium to enhance concentration and separation. Alternately, the sample may be treated with a non-polar solvent to concentrate nucleic acid for hybridization.

Infectious diseases may be diagnosed by the method of the present invention. In the method, a biological sample from an individual is assayed for nucleic acid from a pathogenic organism responsible for the disease. Genetically inherited diseases may be detected by the method using a nucleic acid probe for the disease. A biological sample from an individual may, for example, be contacted with restriction enzyme to form nucleic acid fragments which are measured by the method of the present invention.

The present invention comprises kits for diagnosis of disease. The kits comprise a cartridge with support medium and ionic salts and buffers. The cartridge is capable of being placed in the device of the present invention in contact with the means for applying direct and alternating electric fields. The kit also comprises hybridization probes for hybridization assay of the nucleic acid specific for one or more diseases. Preferably, the hybridization probes comprise a signal generating system whereby the probe may be observed.

BRIEF DESCRIPTION OF THE DRAWINGS

Other advantages of the present invention will become apparent when taken in view of the following illustrations in which:

FIG. 2 shows a preferred embodiment of the device of the present invention comprising removable cartridge with support medium; and FIG. 3 shows an expanded view of the cartridge of the present invention.

DETAILED DESCRIPTION OF THE PREFERRED EMBODIMENTS

Figure 1:
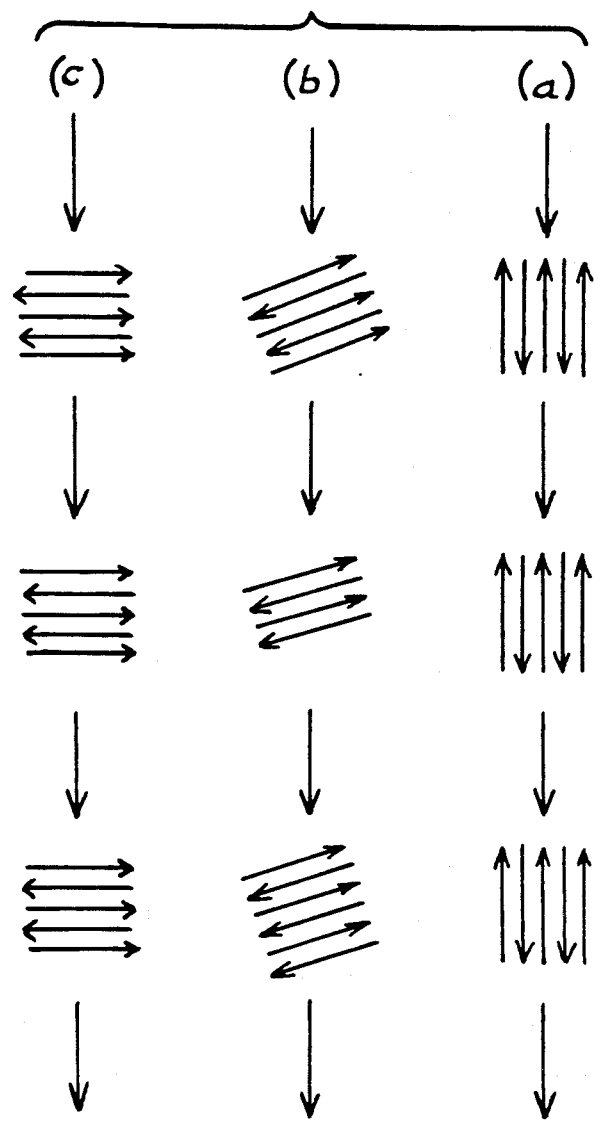
FIG. 1 shows the time phase diagram of the applied fields of the present invention.
Figure 4:
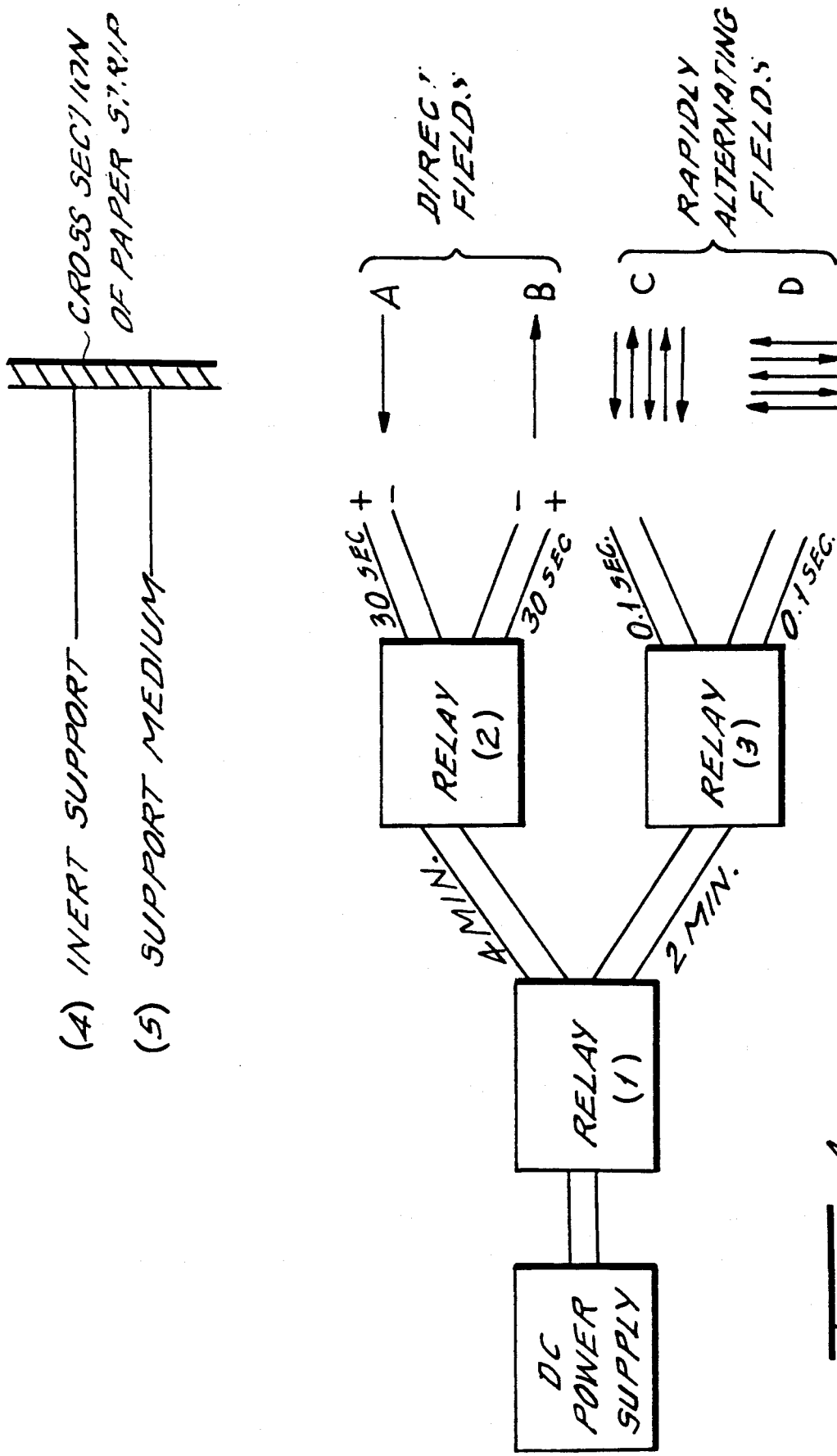
FIG. 4 shows switching mechanism for delivering direct field and rapidly alternating field to a cartridge from a single DC power supply wherein the cartridge is a paper strip comprised of inert support and support medium.

Abbreviations used: DNA, deoxyribonucleic acid; RNA, ribonucleic acid; nucleic acid, any RNA or DNA; DC, direct current; AC, alternating current.

The present invention is directed to a device and method for improved hybridization assays which are especially useful for diagnosis of diseases. The device and method allow separation and resolution of probe from hybrid and other components to which it is artifactually bound during assay. As a result, true hybrids are measured and improved diagnoses are possible.

The device of the present invention may be used in hybridization assays to improve separation of artifactual probe from other nucleic acids and components in a reaction mixture. The device comprises a support medium capable of conducting an electrical current and means for maintaining both direct and alternating electric current applied to the support medium. The support medium is preferably comprised of one or more meshlike polymeric matrix materials which are inert and of a pore size which causes separation of molecules of different size as they pass through. Preferred supporting materials comprise agarose, polyacrylamide, cellulose acetate, dextran, gelatin and agar, most preferably agarose. Other electrophoretic supporting media known in the art may likewise be employed. The support medium may comprise solutions of ionic salts and buffers suitable for allowing an electric field to be maintained and to standardize separation conditions. Ionic salts and buffers to enhance hybridization reactions may also be present. In certain embodiments of the invention, the support medium may comprise one or more membrane sheets. The sheets are of controlled pore size and permit selective passage of components depending on size of component. They are therefore useful in concentration and purification of biological specimen and reaction mixtures on the support medium.

Although it is not intended that the scope of the present invention be limited by any particular mechanism, it is helpful in describing the invention to set forth the apparent chemical reactions which occur during hybridization of the probe. Thus, it appears that two kinds of binding occur between probe and components in the reaction mixture. There is, on the one hand, reaction between complementary base pairs which results in true double-stranded hybrid comprised of probe and target nucleic acid. On the other hand, probe also binds non-specifically to reactive sites other than well-matched base pairs in the sample DNA or in other components of the sample. This is artifactual binding. Probe may be bound non-specifically to other nucleic acid entities such as other single-stranded nucleic acid, double-stranded nucleic acid or aggregates of single- or double-stranded nucleic acid. The non-specifically bound probe may also be bound to the hybrid itself. In addition, the probe may bind to other components of the biological sample such as proteins, polysaccharides, cell components or other biopolymers.

However, non-specifically bound probe and probe specifically bound in the hybrid cannot be distinguished since the label that is measured is the same on both. The labeled entity which is observed is apparently hybrid of probe and target nucleic acid, but may be in reality only an interference from non-specifically bound probe. Therefore, non-specifically bound probe gives erroneous results in the form of false positives.

In the device of the present invention, this non-specifically bound probe is separated from true hybrid so that only true hybrid is observed. This separation is achieved by applying alternating electric fields to the hybrid on a support medium. Application of this alternating field at the correct temperature results in the selective disruption of non-specifically bound probe. This probe will subsequently separate from the truly hybridized probe upon re-application of the direct electric field. Improved measurements result.

The device of the present invention preferably comprises a temperature regulating means for purpose of maintaining correct temperature of the support medium while alternating electric field is applied. Most preferably, regulating means is a temperature detection thermocouple which is placed in the support medium and to the support medium. In this way, voltage is increased or decreased in accordance with temperature needs of the medium and optimal energy requirements for disruption of non-specific bonds and separation of hybrid.

In certain embodiments, the device may comprise a hybridization chamber in addition to a separation chamber. In these embodiments, support medium in the hybridization chamber may also be comprised of ionic salts and buffers for enhancing hybridization.

Alternatively, hybridization may occur in a hybridization container in a hybridization chamber without support medium. The hybridization chamber may comprise, for example, small tubes or a plate with wells. In this embodiment, hybridized sample may be transferred to support medium, by means of a multi-tipped pipette. Most preferably support medium is placed into the sample itself and both sample and support medium are then applied to an inert surface, paper, for example, most preferably paper strips. In this embodiment the paper strip with attached support medium and sample is then placed in the separation chamber where extraneous probe is washed away by means of applied electric fields.

Means for agitation during hybridization may also be provided in the hybridization chamber. A controlled speed rocking mechanism, for example, may be provided.

The device of the present invention may comprise, in addition, surface of inert material, preferably positively charged membranes, nitrocellulose or nylon, for example, in contact with the support medium. The separated hybrid is transferred to the inert surface, as by application or direct current, and is measured on the surface. In certain embodiments, the inert surface comprises one or more strips of material embedded in the support material and essentially parallel to the directional axis of applied direct field and hence migration path of probe and hybrid. In these embodiments, the hybrid is focused on the inert surface in a highly concentrated spot. In other embodiments, the inert surface is a plane of material layering essentially the entire plane of the support medium. In these embodiments, separated hybrid and probe are transferred as bands to the inert surface. After transfer, the hybrid on the inert surface is measured by means of signal generating system on the specifically-bound probe. This system may be a conventional biotin-avidin system, a chromophoric system such as enzymatic system, catalase or peroxidase, for example, or a fluorescent or other optical system based on modified nucleotide components. The signal may be read directly on the inert surface or may be read with appropriate read-out instruments. These and other signal generating systems known to the art may be used to measure hybrid on the inert surface or on the support medium itself.

In preferred embodiments of the present invention, the device comprises, in addition, a means for holding the support medium during hybridization assay. Suitable holders include, for example, horizontal trays or vertical slabs. Most preferably, the holder comprises at least one removable component, most preferably a disposable cartridge in which the support medium has been situated. In embodiments utilizing paper strips, the holder may be a comb of the type commonly used with electrophoretic equipment. The cartridge is of a configuration which allows it to be easily separated from the holder. After the support medium has been used for an assay, the cartridge may be replaced by a cartridge containing fresh medium for further assays on the same holder. Before being placed in the device, the cartridges are supplied with support medium and salt solutions necessary for separation or hybridization under carefully controlled conditions so that variables, such as polymer density, thickness of layer and concentration of salts, are uniform. Certain inaccuracies of measurement may thus be avoided. The cartridges may be maintained, as with hermetically sealed packing material, under sterile moisture-controlled conditions until ready for use in the holder. The cartridges and support medium amy be comprised of inexpensive material and so may be disposable. When placed in the device, the cartridge is situated so as to be in the path of both direct and alternate electric fields. The device may comprise one or more chambers for accommodation of cartride. Thus, the device may comprise a hybridization chamber and a separation chamber and cartridges may be removably placed in each chamber.

The device of the present invention is especially useful for diagnosis of disease in an individual. A biological sample from the individual, preferably blood, urine, feces, tears, saliva or nasal secretion, is contacted with hybridization probe capable of reacting with nucleic acid which indicates a particular disease.

In the case of infectious diseases, the nucleic acid is from a pathogenic organism which is the causative agent of the disease. Examples of pathogenic organisms which may be assayed by the method and device of the present invention include bacteria, viruses, protozoan parasites and yeasts. Included are certain widespread diseases such as malaria, chagas disease, gonorrhea, herpes, hepatitis and acquired immune deficiency syndrome (AIDS). Other diseases caused by pathogenic organisms which a hybridization probe is known may likewise be diagnosed.

In the case of genetic disorders or autonomic disease, the nucleic acid in the sample originates from the patient. The sample may be treated with restriction enzymes to produce fragments of different sizes. These fragments may be separated by size, hybridized and measured on the device of the present invention. Genetic disorders which may be thus analyzed include, for example, sickle-cell anemia, alpha or beta thalassemia, phenylketonuria and hemophilia.

The device is especially useful for testing biological products such as cell cultures, blood products or vaccines for contamination by organisms such as mycoplasma, viruses such as HLTV III and hepatitis.

In the method of the present invention, the sample comprising hybrid and non-specifically bound nucleic acid is placed on a support medium comprised of a mesh-like polymeric matrix material such as is generally used in electrophoretic methods, preferably blood, urine, feces, tears, saliva or nasal secretion. Preferably the support medium is agarose. Other suitable media include polyacrylamide, cellulose acetate, dextran, agar and gelatin. Suitable reagents such as ionic salts or buffers may be added to the support medium in order to enhance, stabilize or standardize the intensity and direction of applied electric fields. Other reagents such as heparin may be added to the buffer in order to mask nucleic acid binding sites in the support medium.

The reaction medium is initially suspended in the medium by being placed at one position in a well, for example, on the medium. As the electric fields are applied, the components of the mixture move into the medium through the pores formed by the mesh-like structure of the polymer. This results in separation of components in the support medium.

Direct electric field may be supplied by a conventional power supply or transformer. The direct field is preferably applied for a period of minutes, preferably about one minute to 60 minutes. The actual time may vary depending on reaction conditions, nature of probe and concentration and amounts of interfering components in the sample and temperature achieved.

Potential of the direct field is preferably about 1 volt to 25 volts, most preferably about 5–8 volts per centimeter. The potential which may be applied is determined by the conductivity of the support medium. The intensity of the electric fields is adjusted in order to achieve exactly the desired temperature, which is critical for achieving separation of the non-specifically bound probe. The temperature of the support medium may be maintained uniform by a thermostated heating means, most preferably or a thermocouple probe attached to a microprocessor for delivering voltage to the medium.

Alternating electric field is applied to the support medium from commonly available industrial or domestic electric power supplies. Frequency may be the usual 60 cycles/second or other commonly available frequency. It is the purpose of the alternating electric field to impose rapid oscillatory motion on the aggregate in order to rupture the artifactual bonding of probe. The released probe is then free to migrate in the direction of the applied direct field.

The time of application of alternating field is determined by the amount of interfering nucleic acid components and other natural components of the biological specimen being analyzed and the amount of oscillatory motion needed to raise the temperature and break artifactual bonding.

Alternating electric field and direct electric field are applied preferably sequentially to the reaction mixture on the support medium. Thus, in preferred embodiments of the invention, direct current is first applied to the support medium and the reaction mixture. Under the influence of the direct current, the components of the biological specimen will begin to migrate in the direction of applied field. Then, in this embodiment, alternating electric field is applied for a period of time, preferably about one to 60 minutes, most preferably about 20 to 30 minutes to rupture artifactual bonding. Direct current is then applied to cause the separated probe to migrate in a separate band away from other components of the reaction mixture. The alternating and direct fields may be applied again as many times as necessary to resolve components of the mixture. In other embodiments of the present invention, direct and alternating currents are applied at the same time, so that rupturing of bonds and separation of bands occur simultaneously. Thus, for example, two pulsating power sources alternating between DC pulses and AC pulses may be applied. Most preferably, switching between DC and AC pulses would occur in about 0.5 second intervals.

FIG. 1 illustrates the axes on which the fields may be applied. Axis is defined as the line along which the electric potential of the field is maintained. In FIG. 1(a) the axis of the direct field and the alternating field are essentially the same. In FIG. 1(b) the axes are at an angle to each other and in FIG. 1(c) the axes are essentially perpendicular. In certain embodiments, the axis of the alternating electric field may be rotated either between applications of direct field or while direct field is being applied.

In preferred embodiments of the invention, sample is treated with hybridization probe to form a reaction mixture which is placed on the medium where hybrid and non-specifically bound probe are separated. A hybridization container comprised of multiple wells may, for example, be provided for hybridization. The hybridization container may be located in a chamber in the device itself. Hybridized sample may be transferred to support medium by means of a multi-tipped pipette. Preferrably hybridized sample and support medium are mixed in the chamber, to a multi-well plate, for example, contacted with an inert surface, preferably paper strips, and then placed in the separation chamber. In other embodiments, hybridization occurs on the support medium. In these embodiments, appropriate salts and buffers are supplied to the medium and temperature may be controlled to provide proper criteria for hybridization. Sample may, for example, be applied to the well of the cartridge, placed in the hybridization chamber of the device where the temperature of medium is controlled and the medium is gently agitated. After hybridization, the cartridge may then be transferred to the separation chamber where direct and alternating fields are applied to separate hybrid. The sample may also be treated prior to hybridization to concentrate components. The sample may, for example, be contacted with a non-polar solvent, phenol, for example, and shaken to form an emulsion. Single-stranded nucleic acid concentrates at the interface between solvents and the emulsion and as a result hybridization occurs at a significantly faster rate (Kohne, D. E., Levison, S. A. and Byers, M. J. (1977)); Biochemistry 16: 5329–5341). The emulsion is placed on the support medium where direct and alternating electric fields are applied. Alternatively, the sample may be concentrated on the support medium by application of direct current. In these embodiments, membrane sheets may be embedded in the medium. The size of holes in the membrane sheets may be chosen to pass selectively or to retard nucleic acid or nucleic acid fragments from other sample components. This procedure is especially useful in analysis of restriction enzyme digest of genetic material.

FIG. 2 illustrates the device of the present invention wherein holder (1) supports removable cartridge (2) containing support medium (3) and suitable ionic salts and buffers for maintaining electric field. A surface of inert material (4) may interface with the supporting medium. Electric field may be applied to support medium by means of suitable power sources. Direct current may be supplied, for example, by batteries or transformers (5) and alternating electric current by conventional power supply (6). Sample wells (7) are located in the cartridge for convenience in loading and aligning sample wells may be comprised of inert material resistant to organic solvents, phenol, for example. In certain embodiments, there may be more than one compartment for cartridges (2) in each holder. The device may also comprise heating means for maintaining temperature of support medium constant during separation. In preferred embodiments of the device of the present invention there is in addition means for applying direct electric field in a direction essentially perpendicular to plane of the support medium and the alternating electric field (8).

FIG. 3 illustrates the cartridge of the present invention comprising support medium (1) and inert surfaces (2). Electric fields are applied by leads (3) (DC) and (4) (AC). Wells (5) and membrane sheets (6) are optional.

The present invention also provides kits for assay of a large number of diseases. The kits comprise one or more cartridges with support medium thereon and hybridization probes suitable for detecting diseases. The cartridge may be placed in the device of the present invention and used to separate and measure hybrid formed by the probe and a biological sample. One cartridge may be used to assay a single speciment for several diseases by use of different probes. Preferably, probes comprise signal generating system for measuring hybrid on inert surface in the cartridge on the support medium.

The present invention is illustrated by the following examples. However, it should be understood that the invention is not limited to the specific details of these examples.

EXAMPLE 1

This example illustrates hybridization assay of blood for lambda phage DNA and separation of hybrid from non-specifically bound probe.

a) Construction of infected blood 10 ul of human blood were added to 10 ng of phage lambda DNA to make infected blood.

b) Protein digestion

Sodium dodecyl sulphate (5.0%), proteinase K (200 ug/ml) and EDTA (5 mM) were added to the blood and digested at 45° C. for 30 minutes.

c) Denaturation

NaOH was added to the digest to denature the DNA. Acetic acid was added to neutralize after denaturation.

d) Hybridization-formation of reaction mixture

Probe, single-stranded DNA labeled with 32 P was added to the denatured digest and was incubated at 65° C. for one hour.

e) Separation of probe from hybrid in reaction mixture

Reaction mixture was loaded on the well of 1.2% agarose gel. DC electric field (6 volts) was applied for 20 minutes. AC electric field (60 cps) was applied for 20 minutes. AC electric field (60 cps) was applied at a 90 degree angle to the direction of direct field for 15 minutes. DC field was applied again in the original direction for 20 minutes.

f) Measurement of hybrid

The gel was dried for 15 minutes and exposed to X-ray film for one hour. Bands were observed on film corresponding to hybrid and separated probe.

EXAMPLE 2

This example illustrates hybridization assay of blood to detect T. cruzi DNA and separation of hybrid from non-specifically bound probe using a paper strip format.

a) to c) Preparation of Sample.

8 samples are prepared according to Example 1, steps a) to c), adding T. cruzi DNA to blood, instead of lambda DNA. Total volume of each sample is 40 ul. Samples are placed in each of 8 wells arranged in standard microtiter (96 well) format.

d) Labeling of Sample.

32 P labeled T. cruzi DNA probe is added to each denatured sample and incubated at 65° C. for ten minutes.

e) Addition of Support Medium 15 ul of 2% agarose at temperature of 65° C. are added to each sample and mixed. (Final concentration of agarose in each sample is 0.4%).

f) Preparation of Paper Strips

A comb comprising 8 thin paper strips spaced in standard microtiter format is introduced into the wells and allowed to sit for 30 seconds so that agarose and sample are absorbed on the paper strips.

g) Washing of Paper Strips

The comb is removed from the wells and introduced into the device of the present invention, said device comprising means for maintaining alternating and direct electric field to agarose on the paper strip. Direct electric field is applied 30 seconds and then rapidly alternating field (0.1 second) is applied for 1 minute. This cycle is repeated for 20 minutes.

h) Measurement of Hybrid

The paper comb is dried for five minutes with a hot-air blower and exposed to X-ray film for several hours. The radioautographic image of specifically hybridized probe is observed on the film.

What is claimed is:

1. A method of separating nucleic acid from substances to which it is bound non-specifically comprising:

a) contacting said nucleic acid and said substances to which it is bound non-specifically with support medium; and applying alternate electric field and direct electric field to said support medium; wherein the direction of said direct field is essentially parallel to the direction of said alternating field.

2. A method of separating nucleic acid from substances to which it is bound non-specifically comprising:

a) contacting said nucleic acid and said substances to which it is bound non-specifically with support medium; and b) applying alternate electric field and direct electric field to said support medium; wherein said direct electric field and said alternating electric field are applied at different times to said support medium.

* * * * *